(12) United States Patent
Sugawara et al.

(10) Patent No.: US 7,652,179 B2
(45) Date of Patent: Jan. 26, 2010

(54) GAS FOR PLASMA REACTION, PROCESS FOR PRODUCING THE SAME, AND USE THEREOF

(75) Inventors: Mitsuru Sugawara, Tokyo (JP); Toshiro Yamada, Tokyo (JP); Tatsuya Sugimoto, Tokyo (JP); Kimiaki Tanaka, Tokyo (JP)

(73) Assignee: Zeon Corporation, Tokyo (JP)

( * ) Notice: Subject to any disclaimer, the term of this patent is extended or adjusted under 35 U.S.C. 154(b) by 20 days.

(21) Appl. No.: 12/007,522

(22) Filed: Jan. 11, 2008

(65) Prior Publication Data

US 2008/0139855 A1    Jun. 12, 2008

Related U.S. Application Data

(62) Division of application No. 10/493,225, filed as application No. PCT/JP02/11360 on Oct. 31, 2002, now Pat. No. 7,341,764.

(30) Foreign Application Priority Data

Nov. 8, 2001   (JP) .............................. 2001-342791
Mar. 22, 2002  (JP) .............................. 2002-081893

(51) Int. Cl.
   *C07C 21/22*   (2006.01)
(52) U.S. Cl. .............. 570/136; 252/79.1; 257/E21.218; 257/E21.252
(58) Field of Classification Search ....................... None
   See application file for complete search history.

(56) References Cited

U.S. PATENT DOCUMENTS

| | | | | |
|---|---|---|---|---|
| 5,665,383 A | * | 9/1997 | Grinstaff et al. | 424/450 |
| 6,534,417 B2 | * | 3/2003 | Stoehr et al. | 438/715 |
| 6,784,111 B2 | * | 8/2004 | Donohoe et al. | 438/710 |
| 2005/0247670 A1 | * | 11/2005 | Yamada et al. | 216/67 |
| 2007/0282142 A1 | * | 12/2007 | Ohmi et al. | 570/124 |

FOREIGN PATENT DOCUMENTS

| | | |
|---|---|---|
| EP | 499984 | 8/1992 |
| JP | 6-338479 | 12/1994 |
| JP | 9-191002 | 7/1997 |
| JP | 11-162960 | 6/1999 |
| JP | 2002-220668 | 8/2002 |
| WO | WO-00/59021 | 10/2000 |
| WO | WO-02/39494 | 5/2002 |

OTHER PUBLICATIONS

R.D. Dresdner, F.N. Tlumac, J.A. Young, Alkali Fluorides as Catalysts in Reactions Involving Unsaturated Fluorocarbons, 1965, Journal of Organic Chemistry vol. 30, pp. 3524-3527 (1965).*
Derwent-ACC- No. 2002-328125, Derwent abstract of US Patent 6,784,111 (2004).*
International Search Report for the corresponding international patent application No. PCT/02/11360, dated Feb. 4, 2003 (Citing References AC-AE).

* cited by examiner

*Primary Examiner*—Allan Olsen
(74) *Attorney, Agent, or Firm*—Edwards Angell Palmer & Dodge LLP

(57) ABSTRACT

A gas for plasma reaction comprising a chainlike perfluoroalkyne having 5 or 6 carbon atoms, preferably perfluoro-2-pentyne. This plasma reaction gas is suitable for dry etching for formation of a fine pattern, for plasma CVD for formation of a thin film, and for plasma ashing. The plasma reaction gas is synthesized by contacting a dihydrofluoroalkane compound or a monohydrofluoroalkene compound with a basic compound.

8 Claims, No Drawings

GAS FOR PLASMA REACTION, PROCESS FOR PRODUCING THE SAME, AND USE THEREOF

This application is a divisional application of U.S. application Ser. No. 10/493,225, filed Nov. 15, 2004, and claims the right of priority under 35 U.S.C. §119 based on Japanese Patent Application Nos. 2001-342791 filed Nov. 8, 2001 and 2002-081893 filed Mar. 22, 2002, which is hereby incorporated by reference herein in its entirety as if fully set forth herein.

TECHNICAL FIELD

This invention relates to a gas for plasma reaction comprising perfluoroalkyne, a process for producing the same, and uses of the same.

The gas for plasma reaction of the present invention is useful for dry etching, for example, in the production of a semiconductor device, for film-formation by a CVD method, and for ashing.

BACKGROUND ART

With the advance in high integration and high performance of semiconductor devices such as VLSI (Very Large Scale Integrated Circuit) and ULSI (Ultra Large Scale Integrated Circuit), technical requirements for a gas for plasma reaction used in the production process of these semiconductor devices are becoming increasingly strict.

As a gas for plasma reaction used in the semiconductor devices, saturated fluorocarbons such as carbon tetrafluoride and perfluorocyclobutane have heretofore been widely used. However, it is said that saturated fluorocarbon gases have a long life in the air, i.e., a life of several-thousand years or more, and exert a considerable influence upon the global warming. Therefore, various novel fluorine-containing compounds have been developed as substitutes for saturated hydrocarbons.

However, in the case when compounds having a carbon-carbon double bond in the molecule such as, for example, perfluoro-1,3-butadiene or perfluorocyclopentene is used for dry etching a silicon compound layer such as a silicon oxide layer, good selectivity to a protective film such as polysilicon film and phoptoresist film has been of ten difficult to obtain under many etching conditions, with the result that fine patterns were difficult to form.

Perfluoroalkyne compounds having a carbon-carbon triple bond are used as raw materials for the production of fluorine-containing polymers, and pesticides and pharmaceuticals. Several processes for the production of such perfluoroalkyne compounds have heretofore been proposed.

For example, a process for synthesizing perfluoro-2-pentyne is described in J. Am. Chem. Soc., vol. 76, p 611 (1954) wherein hexachlorocyclopentadiene is treated with antimony trifluorodichloride to synthesize 1,2-dichloro-3,3,4,4,5,5-hexafluorocyclopentene; and, 2,3-dichloro-1,1,1,4,4,5,5,5-octafluoro-2-pentene as produced as a by-product in this synthetic process is dechlorinated with zinc to give perfluoro-2-pentyne. This process has a problem such that an antimony pentahalide, which is troublesome to handle, must be used for obtaining the raw material (i.e., 2,3-dichloro-1,1,1,4,4,5,5,5-octafluoro-2-pentene), and the yield of perfluoro-2-pentyne is low.

Processes for synthesizing perfluoro-2-pentyne by isomerization of perfluoro-1,2-pentadiene, perfluoro-1,4-pentadiene and perfluoro-1,3-pentadiene are described in J. Chem. Soc. (C), p 454 (1969); J. Org. Chem., vol. 30, p 3524 (1965); and J. Am. Chem. Soc., vol. 81, p 1767 (1961). These compounds used as a raw material are not readily commercially available, and the rates of isomerizing conjugated or non-conjugated carbon-carbon double bonds in these compounds into a carbon-carbon triple bond are low.

It is further described in J. Chem. Soc. (C), p 454 (1969) that perfluoro-2-pentyne was purified using a gas chromatography apparatus. However, the purity of thus-obtained perfluoro-2-pentyne is 96% at the highest. The gas chromatography apparatus cannot be used for purification in an industrial scale.

The above-mentioned synthetic processes and purifying processes for perfluoroalkyne compounds are drawn to synthesis and purification of a perfluoroalkyne compound having a chainlike structure with 5 carbon atoms, namely, perfluoro-2-pentyne. Such a perfluoroalkyne compound with a relatively low molecular weight has a moderate boiling point and good handling properties, and it is expected to be widely used. Thus, it is desired to develop an industrial process for producing this compound.

DISCLOSURE OF THE INVENTION

In view of the foregoing problems of the prior art, an object of the present invention is to provide a novel gas for plasma reaction exhibiting a high selectivity to a material to be etched.

Another object of the present invention is to provide a process for producing industrially advantageously a perfluoroalkyne compound with a high purity and in an improved efficiency.

Thus, in one aspect of the present invention, there is provided a gas for plasma reaction comprising a compound represented by the following formula (1):

$$R^1-C\equiv C-R^2 \tag{1}$$

wherein $R^1$ is fluorine, a perfluoroalkyl group having 1 to 3 carbon atoms or a perfluoroalkenyl group having 2 to 3 carbon atoms, $R^2$ is a perfluoroalkyl group having 1 to 4 carbon atoms, a perfluoroalkenyl group having 2 to 4 carbon atoms, or a perfluoroalkynyl group having 2 to 4 carbon atoms, provided that the number of total carbon atoms in the sum of $R^1$ and $R^2$ is 3 or 4, and $R^1$ and $R^2$ may be the same or different.

In another aspect of the present invention, there is provided a process for producing a gas for plasma reaction comprising a compound represented by the following formula (1):

$$R-C\equiv C-R^2 \tag{1}$$

wherein $R^1$ is fluorine, a perfluoroalkyl group having 1 to 3 carbon atoms or a perfluoroalkenyl group having 2 to 3 carbon atoms, $R^2$ is a perfluoroalkyl group having 1 to 4 carbon atoms, a perfluoroalkenyl group having 2 to 4 carbon atoms, or a perfluoroalkynyl group having 2 to 4 carbon atoms, provided that the number of total carbon atoms in the sum of $R^1$ and $R^2$ is 3 or 4, and $R^1$ and $R^2$ may be the same or different; said process being characterized in that at least one kind of compound selected from compounds represented by the following formula (2) and compounds represented by the following formula (3):

$$R^1-CHF-CHF-R^2 \tag{2}$$

$$R^1-CX=CY-R^2 \tag{3}$$

wherein $R^1$ and $R^2$ are the same as defined in formula (1), and one of X and Y in formula (3) is hydrogen and the other is fluorine, is contacted with a basic compound.

In still another aspect of the present invention, there is provided a process for producing a gas for plasma reaction with a high purity from a crude reaction product containing the compound represented by formula (1), more specifically, by (i) a purifying method wherein the crude reaction product is subjected to fractional distillation in an atmosphere of inert gas of group 18 of the periodic table, or (ii) a purifying method comprising a first step in which the crude reaction product is subjected to fractional distillation to obtain a gas for plasma reaction with a purity of at least 99.9% by volume, and a second step in which residual trace amounts of impurities are removed from the gas obtained in the first step.

In further aspects of the present invention, there are provided a process for producing an electrical or electric part by dry etching using as an etching gas the above-mentioned gas for plasma reaction; a process for forming a fluorocarbon thin film by chemical vapor deposition using the above-mentioned gas for plasma reaction; and an ashing method using the above-mentioned gas for plasma reaction.

BEST MODE FOR CARRYING OUT THE INVENTION

Gas for Plasma Reaction (I) Chainlike Perfluoroalkyne

A gas for plasma reaction of the present invention is characterized by comprising a chainlike perfluoroalkyne represented by formula (1) in the gas for plasma reaction, which has 5 or 6 carbon atoms. The content of the chainlike perfluoroalkyne of formula (1) is usually at least 90% by volume, preferably at least 99% by volume, more preferably at least 99.95% by volume and especially preferably at least 99.98% by volume, based on the total amount of the gas for plasma reaction. When the content of the chainlike perfluoroalkyne is low, the rate of etching and the selectivity to a protective film such as photoresist film and polysilicon film tend to be reduced.

By the term "chainlike perfluoroalkyne" as used in the present invention, we mean a chainlike compound having at least one carbon-carbon triple bond in the molecule. The chainlike perfluoroalkyne of formula (1) includes, for example, those which has a triple bond only at an end of the molecule, a triple bond only at a middle of the molecule, and triple bonds at both of an end of the molecule and a middle thereof. The chainlike perfuoroalkyne may have two or more triple bonds, or have both of a triple bond and a double bond. The number of triple bonds in the chainlike perfluoroalkyne molecule is usually in the range of 1 to 3, and the number of double bonds therein is usually in the range of 0 to 3.

In the compound represented by formula (1), $R^1$ is fluorine, a perfluoroalkyl group having 1 to 3 carbon atoms or a perfluoroalkenyl group having 2 to 3 carbon atoms, $R^2$ is a perfluoroalkyl group having 1 to 4 carbon atoms, a perfluoroalkenyl group having 2 to 4 carbon atoms, or a perfluoroalkynyl group having 2 to 4 carbon atoms, provided that the number of total carbon atoms in the sum of $R^1$ and $R^2$ is 3 or 4, and $R^1$ and $R^2$ may be the same or different.

The above-mentioned perfluoroalkyl group may be either chainlike (including straight chain and branched chain) or cyclic. The perfluoroalkyl group includes, for example, completely fluorinated (i.e., perfluorinated) methyl group, ethyl group, n-propyl group, isopropyl group, n-butyl group, isobutyl group, sec-butyl group, tert-butyl group and cyclobutyl group. The perfluoroalkenyl group includes, for example, perfluorinated ethenyl group (i.e., vinyl group), propenyl group and butenyl group. The perfluoroalkynyl group includes, for example, perfluorinated ethynyl group, propynyl group and butynyl group.

Preferably $R^1$ and $R^2$ are independently selected from perfluoroalkyl groups having 1 to 3 carbon atoms. That is, $R^1$ and $R^2$ are preferably independently selected from a perfluoromethyl group, a perfluoroethyl group and a perfluoropropyl group. More preferably one of $R^1$ and $R^2$ is a perfluoromethyl group and the other is a perfluoroethyl geoup.

As specific examples of the chainlike perfluoroalkyne, there can be mentioned chainlike perfluoroalkynes having a triple bond or bonds only at one end or both ends of the molecule such as perfluoro-1-pentyne, perfluoro-3-methyl-1-butyne, perfluoro-1-penten-4-yne, perfluoro-3-penten-1-yne, perfluoro-2-methyl-1-buten-3-yne, perfluoro-1,4-pentadiyne, perfluoro-1-hexyne, perfluoro-3-hexen-1-yne, perfluoro-4-hexen-1-yne, perfluoro-1-hexen-5-yne, perfluoro-2-methyl-2-penten-4-yne, perfluoro-3-methyl-2-penten-4-yne, perfluoro-1,5-hexadiyne and perfluoro-3-methyl-1,4-pentadiyne; chainlike perfluoroalkynes having a triple bond or bonds only at a middle of the molecule such as perfluoro-2-pentyne, perfluoro-1-penten-3-yne, perfluoro-2-hexyne, perfluoro-3-hexyne, perfluoro-1-hexen-4-yne, perfluoro-2-hexen-4-yne, perfluoro-1-hexen-3-yne, perfluoro-2-methyl-1-penten-3-yne and perfluoro-2,4-hexadiyne; and chainlike perfluoroalkynes having triple bonds at both of an end of the molecule and a middle thereof such as perfluoro-1,3-pentadiyne, perfluoro-1,3-hexadiyne and perfluoro-1,4-hexadiyne.

Of these, chainlike perfluroalkynes having a triple bond or bonds only at a middle of the molecule are preferable. Chainlike perfluroalkynes having a triple bond only at a middle of the molecule and having 5 carbon atoms are more preferable. Perfluoro-2-pentyne is especially preferable, which is a known substance having a boiling point of 5° C. at normal pressure.

These perfluoroalkynes may be used either alone or as a combination of at least two thereof. However, a single use thereof is preferable because a gas for plasma reaction having a uniform composition can be obtained.

(II) Composition of Chainlike Perfluoroalkyne

By the term "a gas for plasma reaction" as used in the present invention, we mean a gas which is produced by the process for producing a gas for plasma reaction, mentioned below, or by other processes, and, is used for a plasma reaction involved, for example, in the production process for a semiconductor device, if desired in the state of being filled in a voluntary vessel. The gas for plasma reaction of the present invention should be broadly construed as including, for example, a mixed gas comprising the above-mentioned gas for plasma reaction having added therein another kind of gas for plasma reaction or a diluent gas, which does not give a substantially harmful influence on the object of the present invention. The mixed gas may be prepared by adding the other kind of gas for plasma reaction or the diluent gas to the above-mentioned gas for plasma reaction, filled in a voluntary vessel; or, by taking a part of the above-mentioned gas for plasma reaction from a voluntary vessel, and filling the gas together with the other kind of gas for plasma reaction or the diluent gas into another voluntary vessel.

The content of the above-mentioned chainlike perfluoroalkyne in the gas for plasma reaction is usually at least 90% by volume, preferably at least 99% by volume, more preferably at least 99.9% by volume, especially preferably at least 99.95% by volume, and most preferably at least 99.98% by volume, based on the total amount of the gas for plasma reaction. When the content of the above-mentioned chainlike perfluoroalkyne is low, the rate of etching and the selectivity to a protective film such as photoresist film and polysilicon film tend to be reduced, as mentioned above.

In some cases, impurity ingredients are present in trace amounts in the gas for plasma reaction of the present invention, which include, for example, air and nitrogen gas derived from a production apparatus, and moisture derived from a solvent, a hygroscopic salt and an alkali which are used for the production of the gas for plasma reaction. The amount of these impurity ingredients should be as small as possible for the following reasons. Firstly, impurities such as nitrogen, oxygen and moisture are dissociated in an apparatus for plasma reaction to form various free radicals (etching species), which greatly influence plasma reaction of the chainlike perfluoroalkyne. Secondly, in the case when the content of nitrogen gas exceeds a certain level, the plasma reaction of the chainlike perfluoroalkyne tends to become polymerization, rather than decomposition of free radicals, thereby to form undesirable polymer deposits. Thirdly, when the chainlike perfluoroalkyne produced is taken from a vessel, the amounts of volatilized nitrogen gas, oxygen gas, moisture and other gases vary with time, and consequently, it becomes difficult to stably carry out the plasma reaction under constant conditions.

Therefore, the total content of nitrogen gas and oxygen gas, which are contained as balance micro gas ingredients in the gas for plasma reaction, is preferably not larger than 200 ppm by volume, more preferably not larger than 150 ppm by volume and especially preferably not larger than 100 ppm by volume, based on the total amount of the gas for plasma reaction. Further, the amount of moisture is preferably not larger than 30 ppm by weight, and especially preferably not larger than 20 ppm by weight, based on the total amount of the gas for plasma reaction.

By the term "content of the chainlike perfluoroalkyne" as used herein, we mean purity in volume standard calculated from weight percent as determined by gas chromatography analysis (hereinafter abbreviated to as "GC analysis" when appropriate) according to an internal reference material method. The above-mentioned total content of nitrogen gas and oxygen gas also means the sum of nitrogen gas content in ppm by volume and oxygen gas content in ppm by volume, which are determined by GC analysis. These contents in volume standard may be said as those in mol standard. The content of moisture is expressed in ppm by weight as determined by the Karl-Fischer method.

The gas for plasma reaction of the present invention may contain at least one kind of perfluorohydrocarbon, other than the chainlike perfluroalkyne, which includes straight-chain or cyclic perfluoroolefins, perfluoroalkanes and perfluorocycloalkanes. However, if these perfluoroolefins, perfluoroalkanes and perfluorocycloalkanes are contained in large amounts, the object of the present invention cannot be achieved. Therefore, the amount of these perfluorohydrocarbons is usually not larger than 30% by weight, preferably not larger than 20% by weight and more preferably not larger than 10% by weight, based on the total amount of the chainlike perfluoroalkyne and the other perfluorohydrocarbons.

The gas for plasma reaction may contain a hydrofluorocarbon in addition to the chainlike perfluoroalkyne for use, for example, as an etching gas. The hydrofluorocarbon is not particularly limited provided that it is a volatile gas, and is usually selected from straight-chain or branched-chain, or cyclic saturated hydrocarbons, at least half number of the hydrogen atoms of which have been substituted with fluorine atoms.

As specific examples of such saturated hydrofluorocarbon gases, there can be mentioned trifluoromethane, pentafluoroethane, tetrafluoroethane, heptafluoropropane, hexafluoropropane, pentafluoropropane, nonafluorobutane, octafluorobutane, heptafluorobutane, hexafluorobutane, undecafluoropentane, tridecafluorohexane, dodecafluorohexane, undecafluorohexane, heptafluorocyclobutane, hexafluorocyclobutane, nonafluorocyclopentane, octafluorocyclopentane and heptafluorocyclopentane. Of these, trifluoromethane, pentafluoroethane and tetrafluoroethane are preferable. These hydrofluorocarbon gases may be used either alone or as a combination of at least two thereof.

The amount of the hydrofluorocarbon used in addition to the chainlike perfluoroalkyne varies depending upon the degree of influence of the gas for plasma reaction upon the material to be etched, but the amount thereof is usually not larger than 50% by mol, preferably not larger than 30% by mol, based on the chainlike perfluoroalkyne.

(III) Process for Producing Chainlike Perfluoroalkyne-Containing Gas for Plasma Reaction The chainlike perfluoroalkyne represented by formula (1) can be produced by a process wherein at least one kind of compound selected from compounds represented by the following formula (2) and compounds represented by the following formula (3):

$$R^1\text{—CHF—CHF—}R^2 \quad (2)$$

$$R^1\text{—CX=CY—}R^2 \quad (3)$$

wherein $R^1$ and $R^2$ are the same as defined in formula (1), and one of X and Y in formula (3) is hydrogen and the other is fluorine, is contacted with a basic compound.

The dihydroalkane compound represented by formula (2) includes a threo-form diastereomer and/or an erythro-form diastereomer when the adjacent two carbon atoms (in the portion of —CHF—CHF—) are asymmetric carbon atoms. The monohydrofluoroalkene compound represented by formula (3) includes a cis-form compound and/or a trans-form compound.

As preferable specific examples of the starting compounds of formulae (2) and (3), there can be mentioned 1,1,1,2,3,4,4,5,5,5-decafluoropentane and 1,1,1,2,3,4,4,5,5,-6,6,6-dodecafluorohexane as compounds of formula (2); and 1,1,1,2,4,4,5,5,5-nonafluoro-2-pentene and 1,1,1,3,4,4,5,5,5-nonafluoro-2-pentene as compounds of formula (3).

The manner for preparing the compound of formula (2) is not particularly limited, and this compound may be either commercially available or produced in the conventional manner. For example, the above-mentioned 1,1,1,2,3,4,4,5,5,5-decafluoropentane can easily be produced by a process wherein tetrafluoroethylene and hexafluoropropylene are subjected to a disproportionation reaction to synthesize perfluoro-2-pentene, and then, the perfluoro-2-pentene is hydrogenated.

The manner for preparing the compound of formula (3) also is not particularly limited, and this compound may be either commercially available or produced in the conventional manner. Preferably, the compound (3) is prepared by a process wherein the compound of formula (2) is contacted with a basic compound to produce the chainlike perfluoroalkyne according to the present invention, and, the compound (3) as produced as an intermediate product is isolated from a reaction mixture.

The compounds of formula (2) and the compounds of formula (3) may be used either alone or as a combination of at least two thereof. When a mixture of the compound of formula (2) with the compound of formula (3) is used, the mixing ratio of the two compounds is not particularly limited.

The basic compound used for the synthesis reaction is not particularly limited, and, as specific examples thereof, there can be mentioned alkali metal hydroxides such as lithium hydroxide, sodium hydroxide, potassium hydroxide, rubidium hydroxide and cesium hydroxide; alkali metal oxides such as sodium oxide and potassium oxide; alkaline earth metal hydroxides such as beryllium hydroxide, magnesium hydroxide, calcium hydroxide, strontium hydroxide and barium hydroxide; alkaline earth metal oxides such as beryllium oxide, magnesium oxide, calcium oxide, strontium oxide and barium oxide; organoalkali metal compounds such as methyllithium, ethyllithium, n-butyllithium, s-butyllithium, t-butyllithium and lithium diisopropylamide; organoalkaline earth metal compounds such as dimethylmagnesium, diethylmagnesium, methylmagnesium chloride, methylmagnesium bromide, ethylmagnesium bromide and phenylmagnesium bromide; organoaluminum compounds such as trimethylaluminum, triethylaluminum, triisobutylaluminum and diethylaluminum chloride; organozinc compounds such as dimethylzinc and diethylzinc; alkali metal alkoxides and alkaline earth metal alkoxides, such as sodium methoxide, sodium ethoxide, sodium propoxide and potassium t-butoxide; alkali metal hydrides and alkaline earth metal hydrides, such as sodium hydride, potassium hydride, calcium hydride, lithium aluminum hydride and sodium borohydride; quaternary ammononium hydroxides such as tetramethylammonium hydroxide and tetrabutylammonium hydroxide; and ammonia.

Of these basic compounds, inorganic basic compounds such as alkali metal hydroxides, alkali metal oxides, alkaline earth metal hydroxides and alkaline earth metal oxides are preferable. Alkali metal hydroxides are more preferable. Potassium hydroxide, rubidium hydroxide and cesium hydroxide are especially preferable. Potassium hydroxide is most preferable.

As mentioned above, readily available raw materials, i.e., the compound of formula (2) and/or the compound of formula (3) and a basic compound are used as essential raw materials. According to the need, auxiliaries such as a reaction medium, washing water and an extracting solvent can be used.

No limitation is imposed to the contacting procedure, the after-treating procedure and the procedure for purifying an objective compound. Preferably, there can be adopted a process wherein the compound of formula (2) and/or the compound of formula (3) are contacted with a basic compound in the presence or absence of a reaction medium, and the thus-obtained reaction liquid is subjected to solid-liquid separation, and the thus-separated liquid (i.e., a crude reaction product) is distilled.

The contact of raw material can be carried out in the presence or absence of a reaction medium, in a homogeneous or heterogeneous (solid-liquid) state, and under heated or non-heated conditions. More preferably, the contact of raw material is carried out in the absence of a reaction medium, in a heterogeneous state, and under heated conditions while being stirred.

If desired, the contact of raw material can be conducted in the presence of a phase transfer catalyst. As specific examples of the phase transfer catalyst, there can be mentioned quaternary ammonium halides such as tetramethylammonium chloride, tetrabutylammononium bromide and methyltrioctylammonium bromide; and quaternary phosphonium halides such as tetrabutylphosphonium bromide and tetraphenylphosphonium bromoide.

In the case when an inorganic basic compound is used as the basic compound and a reaction medium is used, the reaction medium is preferably selected from water; alcohols such as methanol, ethanol, 1-propanol and 2-propanol; and glycols such as polyethylene glycol. These reaction mediums can be used either alone or as a combination of at least two thereof. The amount of reaction medium is usually not larger than 20 times, preferably not larger than 10 times and more preferably not larger than 5 times, of the weight of inorganic basic compound.

The amount of the basic compound is usually in the range of 1 to 5 equivalents, preferably 1.2 to 4 equivalents and more preferably 1.5 to 3.5 equivalents, based on the mol number of hydrogen atoms contained in the raw material compounds represented by formulae (2) and (3).

The reaction temperature is not particularly limited but is usually in the range of 30 to 400° C., preferably 100 to 350° C. and more preferably 150 to 300° C. The reaction time also is not particularly limited but is usually in the range of 0.1 to 20 hours, preferably 0.2 to 15 hours and more preferably 0.3 to 10 hours. The reaction pressure may be either super-atmospheric or sub-atmospheric.

The above-mentioned reaction may be carried out in either batchwise manner or continuous manner. The reaction apparatus is not particularly limited, and apparatuses industrially conventionally used may be used. A stainless steel pressure-resistant reaction vessel is preferably used.

After completion of the reaction, the reaction product as produced can be subjected to an after-treatment by a conventional procedure. In the case when the reaction is carried out in the absence of a solvent, the reaction product as produced is preferably subjected to a solid-liquid separation. The procedure for solid-liquid separation is not particularly limited, and includes, for example, filtration, centrifugation and distillation. Preferably the reaction product is distilled to be thereby separated into a liquid and a solid. The thus-obtained liquid (i.e., a crude reaction product) is distilled under a sub-atmospheric pressure or a super-atmospheric pressure to give an intended chainlike perfluoroalkyne having a purity of at least 90% by volume, preferably at least 99% by volume or higher.

The composition of the above-mentioned crude reaction product varies depending upon the raw materials used and the reaction conditions adopted. For example, in the case when 1,1,1,2,3,4,4,5,5,5-decafluoropentane is used as a raw material, a potassium hydroxide pellet is added and the reaction is carried out under heated conditions while a reaction mixture is stirred, and the reaction mixture is distilled, the resulting crude reaction product comprises perfluoro-2-pentyne (target compound), 1,1,1,2,4,4,5,5,5-nonafluoro-2-pentene, 1,1,1,3,4,4,5,5,5-nonafluoro-2-pentene, 1,1,1,2,3,4,4,5,5,5-decafluoropentane (raw material), and small amounts of other fluorine-containing compounds, the structures of which are difficult to identify.

According to the above-mentioned synthetic process, a chainlike perfluoroalkyne having 5 or 6 carbon atoms used as a gas for plasma reaction of the present invention can be obtained. However, the synthetic process itself can be adopted for the synthesis of chainlike perfluoroalkynes having more carbon atoms, i.e., chainlike perfluoroalkynes wherein each of $R^1$ and $R^2$ in formula (1) is a perfluorohydrocarbon group having up to 6 carbon atoms.

Among the gases for plasma reaction of the present invention, those which have an especially high purity, more specifically, the following gases (i), (ii) and (iii) are preferably prepared by the following purifying methods (1), (2) and (3).

(i) A gas containing at least 99.9% by volume, based on the total amount of gas for plasma reaction, of the chainlike perfluoroalkyne represented by formula (1).

(ii) A gas wherein the total content of nitrogen gas and oxygen gas that are contained as micro ingredients in the gas for plasma reaction is not larger than 200 ppm by volume based on the total volume of gas for plasma reaction.

(iii) A gas wherein the content of moisture is not larger than 30 ppm by weight based on the total amount of the gas for plasma reaction.

(1) A purifying method wherein the above-mentioned crude reaction product is fed to a fractionating column where the crude reaction product is subjected to fractional distillation (hereinafter referred to as "first purifying method").

(2) A purifying method wherein the above-mentioned crude reaction product is subjected to fractional distillation in an atmosphere of inert gas of group 18 of the periodic table (hereinafter referred to as "second purifying method").

(3) A purifying method comprising two steps wherein, in a first step, the above-mentioned crude reaction product is subjected to fractional distillation to obtain a chainlike perfluoroalkyne fraction having a purity of at least 99.9% by volume, and then, in a second step, residual trace impurities are removed from the product obtained in the first step (hereinafter referred to as "third purifying method").

The first, second and third purifying methods will be described specifically by reference to perfluoro-2-pentyne.

In the first purifying method, the above-mentioned crude reaction product is fed to a fractionating column where the crude reaction product is subjected to fractional distillation whereby perfluoro-2-pentyne having a purity of at least 99.9% by volume can be obtained.

To efficiently remove ingredients having a boiling point analogous to that of perfluoro-2-pentyne, the fractionating column used usually has a theoretical plate number of at least 30, preferably at least 50. The distillation is carried out usually at a pressure of −0.5 atmospheric pressure as gauge pressure or higher, preferably in the range of normal pressure to 10 atmospheric pressure as gauge pressure. The reflux ratio is not particularly limited, and can be appropriately chosen depending upon the capacity of the fractionating column. The reflux ratio is usually at least 2, preferably at least 5. The fractional distillation can be carried out either in a batchwise manner or a continuous manner. The fractional distillation can also be carried out in the presence of an extraction solvent, i.e., as extractive distillation.

Withdrawal of fractions can be carried out while the temperature of the top of fractionating column is controlled. The temperature of the top of fractionating column may be controlled to a temperature equal to or in the vicinity of the boiling point (which varies depending upon the pressure) of perfluoro-2-pentyne used as a gas for plasma reaction.

The moisture contained in the crude reaction product is azeotropically removed as the first fraction, or remains as residue, and therefore, the moisture content in the perfluoro-2-pentyne fraction can be reduced to not larger than 30 ppm by weight. Other organic impurities can be removed by utilizing the boiling point difference from perfluoro-2-pentyne.

A perfluoro-2-pentyne gas having a purity of at least 99.9% by volume can be obtained by the first purifying method, but, to obtain a perfluoro-2-pentyne gas having a higher purity and containing reduced amounts of nitrogen gas, oxygen gas and moisture, the second purifying method and the third purifying method are preferably adopted, which are specifically described as follows.

The second purifying method for removing the above-mentioned impurities to give a high-purity gas for plasma reaction containing at least 99.9% by volume of perfluoro-2-pentyne is characterized as conducting fractional distillation of the above-mentioned crude reaction product in an atmosphere of inert gas of group 18 of the periodic table.

The inert gas of group 18 is not particularly limited, and, as specific examples thereof, there can be mentioned helium, neon, argon, krypton, xenon and radon. Of these, helium, neon and argon are preferable. Helium and argon are especially preferable because their solubility in perfluoro-2-pentyne is low and they are commercially readily available. Helium is most preferable. The gas of group 18 may be used either alone or as a combination of at least two thereof.

The procedure for fractional distillation is not particularly limited provided that the fractional distillation is carried out in an atmosphere of inert gas of group 18. To efficiently remove ingredients having a boiling point analogous to that of perfluoro-2-pentyne, the fractionating column used usually has a theoretical plate number of at least 30, preferably at least 50. The distillation is carried out usually at a pressure of −0.5 atmospheric pressure as gauge pressure or higher, preferably in the range of normal pressure to 10 atmospheric pressure as gauge pressure. The reflux ratio is not particularly limited, and can be appropriately chosen depending upon the capacity of the fractionating column. The reflux ratio is usually at least 2, preferably at least 5. The fractional distillation can be carried out either in a batchwise manner or a continuous manner. The fractional distillation can also be carried out in the presence of an extraction solvent, i.e., as extractive distillation.

Withdrawal of fractions can be carried out while the temperature of the top of fractionating column is controlled. The temperature of the top of fractionating column may be controlled to a temperature equal to or in the vicinity of the boiling point (which varies depending upon the pressure) of the gas for plasma reaction. The moisture contained in the crude reaction product is azeotropically removed as the first fraction, and therefore, the moisture content in the perfluoro-2-pentyne fraction can be reduced to not larger than 30 ppm by weight, preferably not larger than 20 ppm by weight. Other organic impurities can be removed by utilizing the boiling point difference from perfluoro-2-pentyne.

Nitrogen gas and oxygen gas can be removed by a procedure of, for example, (i) substituting the atmosphere within the entire fractionating column with an inert gas of group 18 prior to the fractional distillation; (ii) conducting the total reflux before the withdrawal of fractions and cooling of a reflux condenser is stopped whereby the gases dissolved in the charged liquid are expelled to the outside from the column; or (iii) flowing the inert gas of group 18 through the fractionating column during fractional distillation. The perfluoro-2-pentyne fraction obtained by fractional distillation is filled in a vessel such as bomb in an atmosphere of inert gas of group 18.

The second purifying method is advantageous in that nitrogen gas, oxygen gas, moisture and organic impurities can be simultaneously removed, and a gas for plasma reaction having an extremely high purity, namely, a gas for plasma reaction containing at least 99.9% by volume, based on the total amount of the gas for plasma reaction, of perfluro-2-pentyne and not larger than 200 ppm by volume, based on the total amount of the gas for plasma reaction, of the sum of nitrogen gas and oxygen gas as balance micro gas ingredients can be obtained.

More advantageously, according to the second purifying method, a gas for plasma reaction containing, based on the total amount of the gas for plasma reaction, at least 99.9% by volume of perfluro-2-pentyne, not larger than 200 ppm by volume of the sum of nitrogen gas and oxygen gas as balance micro gas ingredients, and not larger than 30 ppm by weight, preferably not larger than 20 ppm by weight, of moisture can also be obtained.

The third purifying method is characterized as comprising a first step wherein the above-mentioned crude reaction product is subjected to fractional distillation to obtain a chainlike perfluoroalkyne fraction having a purity of at least 99.9% by volume, and a second step wherein residual trace impurities are removed from the product obtained in the first step.

In the first step of the third purifying method, the crude reaction product is subjected to fractional distillation so that the purity of perfluoro-2-pentyne contained in the crude reaction product is enhanced to at least 99.9% by volume, preferably at least 99.95% by volume and more preferably 99.98%by volume. The procedure for the fractional distillation is not particularly limited, but, for example, the procedure as described above as for the second purifying method can be adopted. It is to be noted, however, that it is not essential to conduct the distillation in an atmosphere of inert gas of group 18 in the first step, but the distillation can be conducted in the presence of other gas, for example, nitrogen gas. This is because the gas such as nitrogen gas used in the first step can be removed in the succeeding second step.

The moisture contained in the crude reaction product is azeotropically removed as the first fraction in the first step, and therefore, the moisture content in the perfluoro-2-pentyne fraction can be reduced to not larger than 30 ppm by weight. A predominant part of the organic impurities can be removed by distillation due to the boiling point difference from perfluoro-2-pentyne, and therefore, the purity of perfluoro-2-pentyne can be enhanced to at least 99.9% by volume. If desired, prior to the above-mentioned fractional distillation, a pre-treatment using a treating agent such as a drying agent, a molecular sieve or an adsorbent can be carried out to remove moisture and organic impurities.

By the language "residual trace impurities are removed from the product obtained in the first step" as used in the second step, we usually mean that nitrogen gas and oxygen gas which are contained in the product obtained by fractional distillation in the first step are removed to an extent such that the sum of nitrogen gas and oxygen gas is reduced to not larger than 200 ppm by volume. If desired, trace amounts of residual organic impurities which have not been removed in the first step can be removed in the second step.

The procedure for removing residual trace impurities, i.e., nitrogen gas and oxygen gas, in the second step is not particularly limited, but preferably includes the following three procedures: (i) a procedure wherein reflux is carried out under heated conditions in an atmosphere of inert gas of group 18, (ii) a procedure wherein simple distillation is carried out in an atmosphere of inert gas of group 18, and (iii) a procedure wherein degassing is carried out at a low temperature under a reduced pressure. These procedures (i), (ii) and (iii) may be adopted either alone or as a combination of at least two thereof. Further, if desired, a trace amount of organic impurities can be removed by (iv) a procedure wherein the product obtained in the first step is contacted with a molecular sieve or an adsorbent, prior to or after the procedures (i), (ii) and (iii). These procedures (i), (ii), (iii) and (iv) will be specifically described below.

(i) Procedure Wherein Reflux is Carried Out Under Heated Conditions in Atmosphere of Inert Gas of Group 18

Nitrogen gas and oxygen gas can be removed with a high efficiency from the perfluoro-2-pentyne fraction by conducting reflux in an atmosphere of inert gas of group 18 under heated conditions. As specific examples of the inert gas of group 18, there can be mentioned helium, neon and argon. Helium and argon are preferable because their solubility in perfluoro-2-pentyne is low and they are commercially readily available. Helium is especially preferable.

It is preferable that, prior to the reflux under heated conditions, the entire apparatus is deaerated and flushed with inert gas of group 18, and that inert gas of group 18 is allowed to flow through the apparatus during the course of reflux. It is also preferable that first reflux is conducted in an atmosphere containing nitrogen gas or oxygen gas under heated conditions whereby the nitrogen gas or oxygen gas is expelled from the apparatus by the vapor of perfluoro-2-pentyne, and thereafter, reflux is carried out in an atmosphere of inert gas of group 18 under heated conditions. The vapor of perfluoro-2-pentyne generated by heating is condensed by a condenser provided in the upper part, and the liquefied perfluoro-2-pentyne is flown back to a heated vessel provided in the lower part. To avoid expelling of the vapor, a cooling medium circulated in the condenser is usually maintained at a temperature of not higher than $-5°$ C., preferably not higher than $-10°$ C. and more preferably not higher than $-20°$ C.

If the nitrogen gas or oxygen gas removed by reflux under heated conditions are present in the vicinity of the liquid within the condenser, the nitrogen gas or oxygen gas tends to be undesirably re-dissolved in the liquid. Therefore, it is preferable to temporally stop the cooling of the condenser in the midway of the reflux conducted in an atmosphere of inert gas of group 18 whereby the nitrogen gas or oxygen gas are completely expelled together with a part of the vapor from the apparatus.

The reflux under heated conditions can be conducted at normal pressure or a higher pressure. However, to effectively expel gas ingredients dissolved in the liquid, the reflux is carried out preferably at normal pressure rather than at a higher pressure. The heating procedure may be conventional as popularly adopted in distillation or reactions under heated conditions, and includes, for example, jacket heating, reboiler heating and internal coil heating. The time for the reflux under heated conditions can be appropriately chosen depending upon the amount of the liquid charged for reflux, the amount of the condensed liquid, and the capacity of the condenser, but is usually at least one hour, preferably at least 3 hours.

(ii) Procedure Wherein Simple Distillation is Carried Out in an Atmosphere of Inert Gas of Group 18

After the reflux is carried out under heated conditions in an atmosphere of inert gas of group 18 by the above-mentioned procedure (i) for a stated period of time, the liquid obtained by condensation within the condenser can be taken into another vessel without flowing back into the vessel in which the liquid is initially charged. This procedure is advantageous to avoid the heat deterioration of the perfluoro-2-pentyne occurring in the vessel in which the liquid is initially charged. This procedure can be said as a procedure wherein simple distillation is carried out in an atmosphere of inert gas of group 18. This procedure can be carried out in a manner similar to that in the above procedure (i) without use of s special apparatus and a special operation.

(iii) Procedure Wherein Degassing is Carried Out at a Low Temperature Under a Reduced Pressure In this procedure (iii), the fraction containing nitrogen gas or oxygen gas, obtained in the first step, is allowed to be maintained under a reduced pressure at a low temperature whereby the gaseous ingredients are expelled. The temperature at which the fraction is maintained is preferably not higher than $0°$ C., more preferably not higher than $-20°$ C. If the operation is carried out at a temperature higher than 0° C., but not higher than normal temperature, the amount of perfluoro-2-pentyne volatilized under the reduced pressure and expelled from the apparatus becomes undesirably large. A trap for cryogenic separation is preferably provided in the pressure-reducing line for recovering perfluoro-2-pentyne. The operation is carried out usually under a pressure in the range of 5 to 200 mmHg, preferably 20 to 50 mmHg.

To enhance the efficiency of degassing, the entire liquid can be shaken or exposed to ultrasonic wave. When the fraction is maintained under a reduced pressure for a long period time, the degree of degassing is large, but, evaporation loss of perfluoro-2-pentyne is undesirably increased. Therefore, the time for which the fraction is maintained under a reduced pressure is usually in the range of 10 seconds to 5 minutes, preferably 30 seconds to 2 minutes. The degassing under a reduced pressure can be carried out intermittently, i.e., can be repeated several times. After the fraction is maintained under a reduced pressure, the vessel can be closed as it is, or an inert gas of group 18 can be introduced into the vessel until the pressure reaches normal pressure, to avoid the contact of the deaerated fraction with nitrogen gas or oxygen gas.

(iv) Procedure Wherein the Fraction is Contacted With Molecular Sieve or Adsorbent This procedure is adopted preferably in combination with the above-mentioned procedure (i), (ii) or (iii) to remove organic impurities and give a gas for plasma reaction having an extremely high purity. The removal of organic impurities can be effected by contacting the perfluoro-2-pentyne fraction with a molecular sieve, or an adsorbent such as active carbon or alumina.

The molecular sieve used is not particularly limited, and can be appropriately chosen from many kinds of commercially available molecular sieves. Molecular sieve 3A and molecular sieve 13X (available from Wako Pure Chemical Industries Co., Ltd.) are preferable. Molecular sieve 13X is especially preferable. As alumina, active alumina having a low crystallinity prepared by heat-dehydration of alumina hydrate is preferable. As an example thereof, there can be mentioned alumina catalyst N611N (available from Nikki Chemical Co., Ltd.).

As examples of active carbon, there can be mentioned active carbons prepared from vegetables such as wood, sawdust, charcoal, coconut shell coal, palm core coal, and charcoal residue of combustion; active carbons prepared from coals such as peat, lignite, brown coal, pitch coal and anthracite; active carbons prepared from petroleum materials such as petroleum residue, sulfate sludge and oil carbon; and active carbons prepared from synthetic resins. Particulate active carbon (crushed coal; for example, available from Kishida Kagaku K.K.) is preferably used.

By the above-mentioned purifying method comprising the first step wherein the above-mentioned crude reaction product is subjected to fractional distillation to obtain a chainlike perfluoroalkyne fraction having a purity of at least 99.9% by volume, and the second step wherein residual trace impurities such as nitrogen gas and oxygen gas are removed from the product obtained in the first step, the following high-purity gases for plasma reaction can be obtained:

(i) a gas for plasma reaction wherein the content of perfluoro-2-pentyne is at least 99.9% by volume, and the total content of nitrogen gas and oxygen gas that are contained as balance micro ingredients in the gas for plasma reaction is not larger than 200 ppm by volume, based on the volume of the gas for plasma reaction.

(ii) a gas for plasma reaction wherein the content of perfluoro-2-pentyne is at least 99.9% by volume, the total content of nitrogen gas and oxygen gas that are contained as balance micro ingredients in the gas for plasma reaction is not larger than 200 ppm by volume, and the content of moisture is not larger than 30 ppm by weight, based on the amount of the gas plasma reaction, (iii) a gas for plasma reaction wherein the content of perfluoro-2-pentyne is at least 99.95% by volume and the total content of nitrogen gas and oxygen gas that are contained as balance micro ingredients in the gas for plasma reaction is not larger than 200 ppm by volume, based on the volume of the gas for plasma reaction, and (iv) a gas for plasma reaction wherein the content of perfluoro-2-pentyne is at least 99.95% by volume, the total content of nitrogen gas and oxygen gas that are contained as balance micro ingredients in the gas for plasma reaction is not larger than 200 ppm by volume, and the content of moisture is not larger than 30 ppm by weight, based on the amount of the gas plasma reaction.

(IV) Use of Gas for Plasma Reaction

The gas for plasma reaction of the present invention is used for applications involving plasma reaction such as dry etching, chemical vapor deposition (hereinafter abbreviated to as "CVD" when appropriate) and ashing. However, the applications are not limited thereto. The gas for plasma reaction of the present invention is especially useful for dry etching.

(1) Dry Etching

The dry etching using the gas for plasma reaction of the present invention means a technique for etching a substrate such as a metal part to form a highly integrated minute pattern thereon, for example, in the process of making a semiconductor device. The substrate to be etched includes, for example, a glass substrate, a silicon single crystal wafer and a gallium-arsenic substrate, which have a thin film layer comprised of a material to be etched, on the surface.

As specific examples of the material to be etched, there can be mentioned silicon oxide, silicon nitride, aluminum, tungsten, molybdenum, tantalum, titanium, chromium, chromium oxide and gold. As the substrate, a silicon wafer having a silicon oxide thin film or an aluminum thin film is advantageously used. In the case when the material to be etched is silicon oxide, a photoresist layer or a polysilicon layer as a protective layer is preferably formed on the silicon oxide.

In the dry etching using a gas for plasma reaction of the present invention, plasma having a high density of at least $10^{10}$ ions/cm$^3$ is usually generated. A plasma density in the range of about $10^{10}$ to $10^{13}$ ions/cm$^3$ is preferable for manifesting the maximum performance of plasma and forming a minute pattern. As an apparatus for generating plasma, conventional apparatuses utilizing a reactive ion etching system such as a parallel flat plate type or a magnetron type are generally not suitable for obtaining plasma having the above-mentioned high density. Preferably a helicon wave type and a high-frequency induction type are employed for generating plasma having the above-mentioned high density.

The pressure at which the dry etching is carried out is not particularly limited, but, the above-mentioned etching gas is introduced usually in a vacuumed etching apparatus so that the inner pressure reaches a pressure in the range of about 10 to $10^{-5}$ Torr, preferably about $10^{-2}$ to $10^{-3}$ Torr.

The temperature that a substrate to be etched reaches during etching is usually in the range of 0° to 300° C., preferably 600 to 250° C. and more preferably 800 to 200° C. The temperature of substrate may be controlled, for example, by cooling, or may not be controlled. The time for an etching treatment is in the range of about 10 seconds to about 10 minutes. But, a high rate etching can be adopted for a gas for plasma reaction of the present invention, and therefore, etching can be conducted in the range of 10 seconds to 3 minutes, which is highly efficient in productivity.

(2) Chemical Vapor Deposition (CVD)

By the term "CVD" using a gas for plasma reaction of the present invention, as used herein, we mean a technique for activating and polymerizing a chainlike perfluoroalkyne by plasma discharge to thereby form a thin polymer film on a substrate to be treated. The process in which the thin polymer film is formed cannot be definitely elucidated, but, it is presumed that a chainlike perfluoroalkyne is subjected to polymerization as well as decomposition under plasma dissociating conditions. The plasma CVD can be effected under conditions, varied from plasma density and other conditions under which the above-mentioned dry etching is conducted, and can also be carried out using a mixture of a gas for plasma reaction of the present invention with another gas.

Articles to be subjected to plasma CVD are not particularly limited. However, plasma CVD is usually applied to a surface of articles and parts to which performances or properties such as electrical insulation, water repellency, anticorrosion, acid resistance, lubricating property and antireflection of light are required in a field of semiconductor production, an electrical or electric field, a precision machinery field or other fields. Preferably it is applied to a surface of articles or parts to which an electrical insulation property is required in a field of semiconductor production or an electrical or electric field.

Plasma CVD is especially suitable for formation of an insulation thin film or an insulation material layer in the production step of a semiconductor device. As specific examples of the thin film formed by plasma CVD, there can be mentioned an inter-laminar insulation thin film on an aluminum metal wiring, and a final passivation film for protecting elements.

As methods for plasma CVD, hitherto known methods can be adopted, which include, for example, the method described in Japanese Unexamined Patent Publication No. H9-237783. The plasma generating conditions usually adopted are as follows. High-frequency (RF) output power: 10 W to 10 kW, temperature of article to be treated: 0° C. to 500° C., pressure: 0.1 milli-Torr to 100 Torr. Thickness of the formed thin film is usually in the range of 0.01 to 10 μm.

As an apparatus used for plasma CVD, a parallel flat-plate type CVD apparatus is generally used. However, a microwave CVD apparatus, an ECR-CVD apparatus and high-density plasma CVD apparatuses including a helicon wave type and a high-frequency induction type can also be used.

Irradiation with ultraviolet, for example, by a low-pressure mercury lamp can be carried out for promoting dissociation of a gas for plasma reaction or mitigating a harmful influence on the article to be treated. Irradiation with ultrasonic waves of an article to be treated or a reaction space can also be carried out.

(3) Ashing

By the term "ashing" using a gas for plasma reaction of the present invention, as used herein, we mean a technique for activating a chainlike perfluoroalkyne by plasma discharge using a gas comprising said gas for plasma reaction, thereby ashing and removing contaminant substances present within a chamber of an etching apparatus or a CVD apparatus. The ashing also includes removal of contaminant substances by activated species from a surface of an article to be etched or subjected to CVD, and polishing a surface of an article to be treated whereby the surface is made smooth.

The gas for plasma reaction is especially effectively used for removing an obstructive polymer deposited within a chamber of an apparatus, removing an oxide film from a substrate for a semiconductor device, and separating a resist from a semiconductor device. Occurrence of activated species due to plasma decomposition is required for the plasma ashing, and therefore, the conditions for a plasma reaction should be appropriately chosen.

EXAMPLES

The invention will now be described specifically by the following working examples that by no means limit the scope of the invention.

In these examples, purity (%) of perfluoro-2-pentyne and contents (ppm) of nitrogen gas and oxygen gas are values as measured by GC analysis and expressed by volume unless otherwise specified. Moisture content (ppm) is a value as measured by the Karl-Fischer method and expressed by weight.

GC analysis of perfluoro-2-pentyne was carried out according to the following specifications.

Instrument: HP6890 available from Hewlett-Packard Co.
Column: Ultra-Alloy+−1(s)(length: 60 m, inner diameter: 0.25 mm, membrane thickness: 0.4 μm)
Column temperature: maintained at a constant temperature of 40° C. for 8 minutes, and then, elevated to 200° C. over a period of 8 minutes
Injection temperature: 200° C.
Carrier gas: helium (flow rate in volume: 1 ml/min)
Detector: FID
Amount of sample: 1 μl
Internal reference material: n-butane GC analysis of nitrogen gas and oxygen gas was carried out according to the following specifications.

Instrument: GC-9A available from Shimadzu Corp.
Column: Packed Column J GC-9A (length: 2 m, inner diameter: 3 mm, column packing: Unibeads C 60/80)
Column temperature: 40° C.
Injection temperature: 150° C.
Carrier gas: helium (flow rate in volume: 50 ml/min)
Detector: TCD In the examples, the selectivity for etching to photoresist was evaluated by comparing the etching rates as measured on silicon oxide ($SiO_2$) and photoresist (PR) under the same etching conditions, and calculating the selectivity to PR by the following equation.

$$\text{Selectivity} = (\text{etching rate on } SiO_2)/(\text{etching rate on PR})$$

The etching rates were measured on two points, namely, at the center of wafer (hereinafter referred to as "center") and at a point (hereinafter referred to as "edge") 65 mm apart outward from the center on a line along a diameter of wafer.

EXAMPLE 1

Synthesis of perfluor-2-pentyne

A Hastelloy autoclave was charged with 394 g (5.97 mol) of a commercially available potassium hydroxide pellet (purity: 85%) and 300 g (1.19 mol) of 1,1,1,2,3,4,4,5,5,5-decafluoropentane (available from E.I. Du Pont.). The content was thoroughly stirred and maintained at 200° C. for 7.5 hours to conduct a reaction. Then the autoclave was cooled, and provided with a trap for distilling and collecting a crude reaction product, and connected to a vacuum pump. The crude reaction product was collected by the trap cooled with liquid nitrogen under a reduced pressure. The yield of the collected crude reaction product was 182.5 g.

GC analysis of the crude reaction product reveled that it contained perfluoro-2-pentyne (target compound), 1,1,1,2,4,4,5,5,5-nonafluoro-2-pentene (reaction intermediate A), 1,1,1,3,4,4,5,5,5-nonafluoropentene (reaction intermediate B) and 1,1,1,2,3,4,4,5,5,5-decafluoropentane (raw material). The yield of the target compound was 20.6% on the basis of the raw material charged, and the total yield of reaction intermediate A and reaction intermediate B was 44.2% on the basis of the raw material charged. The unreacted raw material was mostly decomposed and polymerized, and remained within the autoclave. Therefore, the crude reaction product contained only about 1% by weight of the unreacted raw material.

EXAMPLE 2

Preparation of Gas for Plasma Reaction 1,202 g of a crude reaction product (content of perfluoro-2-pentyne: 31.96%) obtained substantially by the same procedures as described in Example 1 was subjected to fractional distillation using KS type fractionating column (theoretical plate number: 35) at normal pressure. A cooling medium at the top of column and a trap for collecting a distilled fraction were maintained at a temperature of −5 to −10° C., and −78° C., respectively. By the fractional distillation, 264 g of a perfluoro-2-pentyne fraction having a purity of 99.9% (boiling point: 5° C.) was obtained.

EXAMPLE 3

Synthesis of perfluoro-2-pentyne

The procedures described in Example 1 were repeated wherein the reaction time was changed to 5 hours with all other conditions remaining the same. The yield of the thus-collected crude reaction product was 194.8 g. The yield of perfluoro-2-pentyne (target compound) was 22.0%, and the total yield of reaction intermediate A and reaction intermediate B, which were the same as those in Example 1, was 46.2%.

EXAMPLE 4

Synthesis of perfluoro-2-pentyne

The procedures described in Example 1 were repeated wherein the reaction time was changed to 1 hour with all other conditions remaining the same. The yield of the thus-collected crude reaction product was 195 g. The yield of perfluoro-2-pentyne (target compound) was 25.0%, and the total yield of reaction intermediate A and reaction intermediate B, which were the same as those in Example 1, was 44.9%.

EXAMPLE 5

Preparation of Gas for Plasma Reaction 983 g of a collected crude reaction product (content of perfluoro-2-pentyne: 26.6%, total content of reaction intermediates A and B: 67.2%) obtained substantially by the same procedures as described in Example 4 was subjected to fractional distillation using KS type fractionating column (theoretical plate number: 35) at normal pressure. A cooling medium at the top of column and a trap for collecting a distilled fraction were maintained at a temperature of −5 to −10° C., and −78° C., respectively. By the fractional distillation, 80.6 g of a perfluoro-2-pentyne fraction having a purity of 99.6% (boiling point: 5° C.), 50.5 g of a perfluoro-2-pentyne fraction having a purity of 99.9% (boiling point: 5° C.), and 482 g of a fraction of reaction intermediates A and B having a purity of 99.8% (boiling point: 29° C.) were obtained.

EXAMPLE 6

Synthesis of perfluoro-2-pentyne

The procedures described in Example 1 were repeated wherein 245 g (1.06 mol) of the fraction of reaction intermediates A and B obtained by fractional distillation in Example 5 was used, 180 g (2.73 mol) of a potassium hydroxide pellet (purity: 85%) was used, and the reaction time was changed to 7.0 hours. All other conditions remained the same. The yield of the thus-collected crude reaction product was 188.8 g. GC analysis revealed that the yield of perfluoro-2-pentyne (target compound) was 25.6%.

EXAMPLE 7

Synthesis of perfluoro-2-hexyne

A Hastelloy autoclave was charged with 394 g (5.97 mol) of a commercially available potassium hydroxide pellet (purity: 85%) and 300 g (0.993 mol) of 1,1,1,2,3,4,4,5,5,6,6,6-dodecafluorohexane. The content was thoroughly stirred and maintained at 200° C. for 7.5 hours to conduct a reaction. Then the autoclave was cooled, and provided with a trap for distilling and collecting a crude reaction product, and connected to a vacuum pump. The crude reaction product was collected by the trap cooled with liquid nitrogen under a reduced pressure. The yield of the collected crude reaction product was 185 g. GC analysis of the crude reaction product reveled that the yield of perfluoro-2-hexyne (target compound) was 20.1% on the basis of the raw material charged.

EXAMPLE 8

Preparation of Gas for Plasma Reaction

A one liter glass round flask, cooled in an ice bath, was charged with 700 g of perfluoro-2-pentyne having a purity of 99.9%, synthesized by the same procedures as mentioned in Example 2, and a boiling stone. The flask was equipped with a Sulzerpack distillation column (theoretical plate number: 55). The liquid part of perfluoro-2-pentyne contained 445 ppm of nitrogen gas and 75 ppm of oxygen gas.

Helium was introduced at a flow rate of 20 ml/min through the upper part of a condenser provided in the fractionating column whereby the inner atmosphere of the fractionating column was substituted with helium. A cooling medium maintained at −15° C. was circulated through the condenser. The flask was immersed in a water bath, and the temperature was elevated to 25° C. and total reflux was conducted for 1 hour. After the one hour's total reflux, the circulation of cooling medium was stopped and the vapor of perfluoro-2-pentyne was allowed to flow upward to the upper part of the condenser. The vapor was taken from the condenser over a period of 3 minutes. Again the cooling medium was circulated through the condenser, and the total reflux was conducted for 1 hour while helium was continuously flown through the column. A fraction was taken at a reflux ratio of 40:1 and collected in a receptacle, which had been previously flushed with helium and cooled to 0° C. Thus, 638 g of a perfluoro-2-pentyne fraction with a purity of 99.98% by volume was obtained (yield: 91.1%).

The above-mentioned perfluoro-2-pentyne fraction was filled in a pressure-resistant closed vessel, maintained at 3° C., while contamination of the fraction with air is avoided. Samples of the fraction were taken from the gaseous part and the liquid part. GC analysis of the samples revealed that the liquid part contained below the limit of detection (i.e., below 10 ppm) of oxygen gas and 34 ppm of nitrogen gas, and the gaseous part contained 15 ppm of oxygen gas and 64 ppm of nitrogen gas. The moisture content in the liquid part was 7% by weight as measured by the Karl-Fischer method.

EXAMPLE 9

Preparation of Gas for Plasma Reaction

First Step:

About 800 g of perfluoro-2-pentyne with a purity of 99.9%, prepared by the same procedures as described in Example 2, was subjected to fractional distillation using a fractionating column with a theoretical plate number of 55 in a nitrogen gas atmosphere at a reflux ratio of 40:1 while the column top was maintained at 5° C. and a cooling medium, maintained at −15° C., was circulated through a condenser equipped in the fractionating column. Thus, perfluoro-2-pentyne having a purity of 99.98% was obtained at a distillation yield of about 90%.

Second Step:

A 500 ml round flask, cooled in an ice bath, was equipped with a cooling condenser having a three-way stopcock, and was charged with a boiling stone and 687 g of perfluoro-2-pentyne, obtained in the first step. A cooling medium maintained at −15° C. was circulated through the cooling condenser, and helium was introduced at a flow rate of 20 ml/min through the three-way stopcock whereby the atmosphere within the flask and the condenser was substituted with helium over a period of 3 minutes. Then the round flask was immersed in a water bath, maintained at 15° C., and perfluoro-2-pentyne was subjected to reflux under heated conditions while helium was continuously introduced into the reflux apparatus so that a helium atmosphere was maintained within the apparatus.

When 20 minutes elapsed, the circulation of cooling medium was stopped and the vapor of perfluoro-2-pentyne was taken through the three-way stopcock over a period of about one minute. Thereafter, the cooling medium was circulated through the condenser to conduct reflux. When 20 minutes elapsed, the procedures of stopping the circulation of cooling medium, taking the vapor of perfluoro-2-pentyne and again circulating the cooling medium was repeated. When 20 minutes elapsed, the water bath was ice-cooled. Thus, 632 g of perfluoro-2-pentyne was collected from the round flask, and the loss of perfluoro-2-pentyne was 55 g. GC analysis of the liquid part revealed that the content of nitrogen gas was 289 ppm and the content of oxygen gas was 70 ppm as measured before the reflux, and the content of nitrogen gas was 28 ppm and the content of oxygen gas was below 10 ppm as measured after the reflux. The moisture content was 13 ppm by weight as measured by the Karl-Fischer method.

EXAMPLE 10

Preparation of Gas for Plasma Reaction

First Step:

By the same procedures as described in the first step of Example 9, 1.2 kg of perfluoro-2-pentyne having a purity of 99.98% was obtained.

Second Step:

1 kg of the perfluoro-2-pentyne obtained in the first step was allowed to circulate through a 150 ml polytetrafluoroethylene column packed with 100 ml of alumina catalyst N611N (available from Nikki Chemical Co., Ltd.) at a space velocity of 10/hour using a liquid feed pump, while the perfluoro-2-pentyne was cooled to −10° C. When 5 hours elapsed, the purity of perfluoro-2-pentyne was measured. The purity was 99.99% by volume.

Then the perfluoro-2-pentyne was subjected to reflux under heated conditions in an argon gas atmosphere in the manner as adopted in the second step of Example 9 using the same apparatus as used in the second step of Example 9. The obtained product was filled in a pressure-resistant vessel. A sample was taken from the liquid part of the product and the moisture content was measured by the Karl-Fischer method. The moisture content was 7 ppm by weight. GC analysis of the gaseous part revealed that the content of oxygen gas was below the limit of detection (i.e., below 10 ppm) and the content of nitrogen gas was 43 ppm.

EXAMPLE 11

Preparation of Gas for Plasma Reaction

First Step:

The procedures as described in the first step of Example 9 were repeated to prepare perfluoro-2-pentyne having a purity of 99.98%.

Second Step:

A 200 ml four-necked flask equipped with a helium gas line, a thermometer, a stirrer, a Claisen simple distillation column, a cooling condenser and a receptacle was charged with 135 g of perfluoro-2-pentyne (purity: 99.98% by volume, content of nitrogen gas: 370 ppm, content of oxygen gas: 73 ppm). The receptacle was cooled to −10° C. The flask was heated to 20° C. in a water bath in a helium gas atmosphere and simple distillation was conducted. The simple distillation was stopped in the midway of ditillation to obtain 77 g of a distilled fraction and 51 g of a residue within the flask. GC analysis of the distilled fraction and the residue revealed that the contents of nitrogen gas and oxygen gas in the distilled fraction were 12 ppm and below 10 ppm, respectively, and the contents of nitrogen gas and oxygen gas in the residue were 30 ppm and below 10 ppm, respectively.

EXAMPLE 12

Dry Etching Using Gas for Plasma Reaction

A silicon wafer having a diameter of 150 mm, on a surface of which a silicon oxide ($SiO_2$) thin film was formed, was set in a helicon wave-type plasma etching apparatus. The inside of the etching apparatus was vacuumed and the gas for plasma reaction, prepared in Example 8, was introduced at a flow rate of 50 sccm. Etching was conducted at a plasma density of $10^{11}$ ions/cm$^3$ while the inside pressure was maintained at 5 milli-Torr.

Similarly, a silicon wafer having a diameter of 150 mm, on a surface of which a photoresist (PR) thin film was formed, was set in a helicon wave-type plasma etching apparatus. Etching was conducted by the same procedures as mentioned above.

The temperature of wafers was not particularly controlled, but was naturally elevated to about 130° C. in the above-mentioned etching steps. The etching time was 60 seconds.

The selectivity for etching to photoresist (PR) was evaluated by comparing the etching rates as measured on silicon oxide (SiO$_2$) and photoresist (PR) under the same etching conditions. The selectivity for etching to PR at the center of wafer was 1.44, and that at an edge of wafer was 1.31. These values were expressed as a relative value provided that the selectivity for etching to PR as measured in Comparative Example 1, below, was 1.

EXAMPLE 13

Dry Etching Using Gas for Plasma Reaction

By the same etching procedures as described in Example 12, etching was conducted wherein the gas for plasma reaction prepared in Example 10 was used instead of the gas for plasma reaction prepared in Example 8 with all other conditions remaining the same. The selectivity for etching to photoresist (PR) was evaluated in the same manner as in Example 12. The selectivity for etching to PR at the center of wafer was 1.50, and that at an edge of wafer was 1.35, as expressed as a relative value provided that the selectivity for etching to PR as measured in Comparative Example 1, below, was 1.

Comparative Example 1

(Dry Etching Using perfluoro-1,3-butadiene for Plasma Reaction)

By the same etching procedures as described in Example 12, etching was conducted wherein commercially available perfluoro-1,3-butadiene having a purity of 99.99% by volume (supplied by Kanto Denka K.K.) was used instead of the gas for plasma reaction prepared in Example 8 with all other conditions remaining the same. The selectivity for etching to photoresist (PR) was evaluated in the same manner as in Example 12. The obtained value for the selectivity for etching to PR was made a reference value for evaluating the selectivities obtained in Examples 12 and 13.

As seen from the comparison of Examples 12 and 13 with Comparative Example 1, a gas for plasma reaction of the present invention exhibits an improved selectivity for etching to photoresist (PR).

EXAMPLE 14

Formation of CVD Insulation Film Using Gas for Plasma Reaction

Plasma CVD of an insulation film was carried out by using the gas for plasma reaction, prepared in Example 8. In CVD, a wafer of partially aluminum-vapor-deposited silicon oxide film was used as a substrate, and a parallel flat-plate type plasma CVD apparatus was used as a plasma CVD apparatus. The CVD was carried out under the following conditions.
Flow rate of high-purity gas for plasma reaction: 40 sccm
Flow rate of argon: 400 sccm
Pressure: 250 milli-Torr
RF output power: 400 W at a frequency of 13.56 MHz.
Substrate temperature: 260° C.

By carrying out CVD under the above-mentioned conditions, a thin film having a thickness of 0.5 µm was formed on the substrate. The thin film had no void and was highly dense and uniform. Adhesion of the film to the substrate was good. The film had a dielectric constant of 2.2.

Comparative Example 2

By the same procedures as described in Example 14, plasma CVD was carried out wherein the same gas as used in Comparative Example 1 was used instead of the gas for plasma reaction, prepared in Example 8, with all other conditions remaining the same. Thus, a thin film having a thickness of about 0.4 µm was formed, which had voids on the surface and was not uniform.

INDUSTRIAL APPLICABILITY

A gas for plasma reaction of the present invention comprising a chainlike perfluoroalkyne having 5 or 6 carbon atoms exhibits an improved selectivity for etching to a substrate to be etched. Therefore, when the gas for plasma reaction is used for dry etching, a fine pattern is advantageously formed. The gas for plasma reaction also exhibits good performance for plasma CVD for the formation of a thin film, and for plasma ashing.

By the above-mentioned process of the present invention, the gas for plasma reaction containing a chainlike perfluoroalkyne having a high purity can be produced industrially beneficially with a high efficiency.

The Invention claimed is:

1. A gas for plasma reaction comprising at least 99.9% by volume, based on the total amount of the gas for plasma reaction, a compound represented by the following formula (1):

$$R^1\!-\!C\!\equiv\!C\!-\!R^2 \qquad (1)$$

wherein $R^1$ is fluorine, a perfluoroalkyl group having 1 to 3 carbon atoms or a perfluoroalkenyl group having 2 to 3 carbon atoms, $R^2$ is a perfluoroalkyl group having 1 to 4 carbon atoms, a perfluoroalkenyl group having 2 to 4 carbon atoms, or a perfluoroalkynyl group having 2 to 4 carbon atoms, provided that the number of total carbon atoms in the sum of $R^1$ and $R^2$ is 3 or 4, and $R^1$ and $R^2$ may be the same or different.

2. The gas for plasma reaction according to claim 1 wherein the content of moisture contained in the gas for plasma reaction is not larger than 30 ppm by weight based on the total amount of the gas for plasma reaction.

3. The gas for plasma reaction according to claim 1 wherein the total content of nitrogen gas and oxygen gas that are contained as balance micro ingredients in the gas for plasma reaction is not larger than 200 ppm by volume based on the total amount of the gas for plasma reaction.

4. The gas for plasma reaction according to claim 3 wherein the content of moisture contained in the gas for plasma reaction is not larger than 30 ppm by weight based on the total amount of the gas for plasma reaction.

5. A gas for plasma reaction comprising at least 99.9% by volume, based on the total amount of the gas for plasma reaction, a compound represented by the following formula (1):

$$R^1\!-\!C\!\equiv\!C\!-\!R^2 \qquad (1)$$

wherein $R^1$ and $R^2$ are independently selected from perfluoroalkyl groups having 1 to 3 carbon atoms, provided that the number of total carbon atoms in the sum of $R^1$ and $R^2$ is 3 or 4.

6. The gas for plasma reaction according to claim 5 wherein the total content of nitrogen gas and oxygen gas that are contained as balance micro ingredients in the gas for plasma reaction is not larger than 200 ppm by volume based on the total amount of the gas for plasma reaction.

7. A gas for plasma reaction comprising at least 99.9% by volume, based on the total amount of the gas for plasma reaction, perfluoro-2-pentyne.

8. The gas for plasma reaction according to claim 7 wherein the total content of nitrogen gas and oxygen gas that are contained as balance micro ingredients in the gas for plasma reaction is not larger than 200 ppm by volume based on the total amount of the gas for plasma reaction.

* * * * *